(12) United States Patent
MacLeod et al.

(10) Patent No.: US 9,241,704 B1
(45) Date of Patent: Jan. 26, 2016

(54) TWO SUTURE ANCHOR

(71) Applicant: Valeris Medical, LLC, Woodstock, GA (US)

(72) Inventors: William Eric MacLeod, Broxton, GA (US); Daniel Brian Lanois, Atlanta, GA (US)

(73) Assignee: Valeris Medical, LLC, Marietta, GA (US)

( * ) Notice: Subject to any disclaimer, the term of this patent is extended or adjusted under 35 U.S.C. 154(b) by 0 days.

(21) Appl. No.: 14/676,429

(22) Filed: Apr. 1, 2015

Related U.S. Application Data

(63) Continuation of application No. 14/526,938, filed on Oct. 29, 2014.

(51) Int. Cl.
*A61B 17/04* (2006.01)

(52) U.S. Cl.
CPC ...... *A61B 17/0401* (2013.01); *A61B 2017/0406* (2013.01); *A61B 2017/0408* (2013.01); *A61B 2017/0445* (2013.01); *A61B 2017/0459* (2013.01); *A61B 2017/0464* (2013.01)

(58) Field of Classification Search
CPC .......... A61B 17/0401; A61B 2017/0414; A61B 2017/0412; A61B 2017/0448; A61B 2017/0427
See application file for complete search history.

(56) References Cited

U.S. PATENT DOCUMENTS

| | | |
|---|---|---|
| 5,037,422 A | 8/1991 | Hayhurst et al. |
| 5,480,403 A | 1/1996 | Lee et al. |
| 5,647,874 A | 7/1997 | Hayhurst et al. |
| 5,720,765 A | 2/1998 | Thal |
| 5,980,558 A | 11/1999 | Wiley |
| 6,146,406 A | 11/2000 | Shluzas et al. |
| 6,517,542 B1 | 2/2003 | Papay et al. |
| 6,641,596 B1 | 11/2003 | Lizardi |
| 6,641,597 B2 | 11/2003 | Burkhart et al. |
| 8,114,128 B2 | 2/2012 | Cauldwell et al. |
| 8,597,328 B2 | 12/2013 | Cauldwell et al. |
| 8,613,756 B2 | 12/2013 | Lizardi et al. |
| 8,663,325 B2 | 3/2014 | Graf et al. |
| 2011/0313453 A1 | 12/2011 | Krumme et al. |

*Primary Examiner* — Katherine M Shi
*Assistant Examiner* — Michael Mendoza
(74) *Attorney, Agent, or Firm* — David L. King

(57) ABSTRACT

A suture anchor has an entry tip and a hollow cylindrical body. The entry tip is integral to a hollow cylindrical body. The entry tip is at a distal end and the body has a proximal end and projections formed on an external surface of the body for retaining the anchor in a pre-drilled hole formed in bone. Four suture openings are formed on the tip at the distal end. Each opening is connected to an internal cavity of the body. The four suture openings are divided into two pairs, a first pair and a second pair. Each first or second pair of two suture openings are recessed in a respective first or second external channel formed in the entry tip. Each pair of two suture openings is configured to receive a suture.

5 Claims, 5 Drawing Sheets

TWO SUTURE ANCHOR

RELATED APPLICATIONS

The present application is a continuation of co-pending U.S. application Ser. No. 14/526,938 filed Oct. 29, 2014 entitled "Improved Two Suture Anchor".

TECHNICAL FIELD

The present invention relates to bone anchor devices for securing soft tissue to a pair of sutures in the device.

BACKGROUND OF THE INVENTION

When soft tissue such as a ligament or a tendon becomes detached from a bone, surgery may be indicated to reattach or reconstruct the tissue. Various fixation devices, including sutures, screws, staples, wedges and plugs have been used in the past to secure soft tissue to bone.

More recently, various types of suture anchors have been developed. The suture anchors are implanted in bone, and suture passed through the soft tissue is secured to the suture anchor. The technique usually requires the surgeon to tie knots in the suture, though various knotless techniques are also available.

Older style bone anchors had an external eyelet to allow the sutures to be fed through after the screw was driven into the bone. This left the eyelet exposed in the soft muscle tissue at a proximal end of the device.

Later versions of bone anchors have the sutures inserted inside the screw tip well inside the bone. This allows the outer end of the screw to stay flush with the cortical bone outer surface. The sutures can pass inside in some hollow screws from near the tip outer surface. Others have the sutures held near the tip and are exterior held between the anchor threads and the bone. In some suture anchor systems, there is a self-driving feature that has a stainless steel punch with a steel tip that can be malleted into the bone. This design leaves the tip end trapped in the bone opening meaning the patient has a small metal tip in his shoulder or knee.

Ideally, the anchor should leave no metal remnants and ideally is able to provide a knotless fixation or hold of the suture on insertion into the bone.

SUMMARY OF THE INVENTION

The present invention achieves all the objectives and more and can achieve these features with a simple push in type anchor or alternatively a threaded anchor that is rotationally screwed into a bone without twisting or entangling the suture when driven into place.

A suture anchor has an entry tip and a hollow cylindrical body. The entry tip is integral to a hollow cylindrical body. The entry tip is at a distal end and the body has a proximal end and projections formed on an external surface of the body for retaining the anchor in a pre-drilled hole formed in bone. The projections can be ribs or threads. Four suture openings are formed on the tip at the distal end. Each opening is connected to an internal cavity of the body. The four suture openings are divided into two pairs, a first pair and a second pair. Each first or second pair of two suture openings are recessed in a respective first or second external channel formed in the entry tip. Each pair of two suture openings is configured to receive a suture. The first external channel and second external channel can cross in an "X" configuration intersecting a central axis of the anchor body. Alternatively, the first external channel can be parallel to the second external channel with both channels being offset a distance from a center axis of the anchor body. In the "X" configuration, one of the first external channel or second external channel is deeper than the other so the received sutures are at or below the external surface of the tip adjacent the channels at an intersection. Each pair of two suture openings can be threaded by a suture such that a suture end or ends of one suture pass and are pulled through the pair of openings holding a portion of the suture lying in one of the first or second external channels and a suture end or ends of another suture cross the other suture passing and pulled through the other pair of openings and a portion of the other suture being held and lying in the other channel, as the end or ends of both sutures pass through the body opening of the suture anchor past the proximal end.

Preferably, the channel depth at the intersection is equal to the thickness of the crossing sutures and the first or second external channel depth adjacent the intersection is equal to the thickness of a suture being held.

In the parallel embodiment, the first and second external channels each extend to a depth so the received sutures are at or below the external surface of the tip. Each pair of two suture openings can be threaded by a suture such that a suture end or ends of one suture pass are pulled through the pair of openings holding a portion of the suture lying in one of the first or second external channels and a suture end or ends of another suture pass and are pulled through the other pair of openings and a portion of the other suture being held and lying in the other channel parallel to the other suture portion, as the end or ends of both sutures pass through the body opening of the suture anchor past the proximal end. Preferably, the first and second channel each has a depth equal to the thickness of the suture being held.

BRIEF DESCRIPTION OF THE DRAWINGS

The invention will be described by way of example and with reference to the accompanying drawings in which.

DETAILED DESCRIPTION OF THE INVENTION

Figure 1:
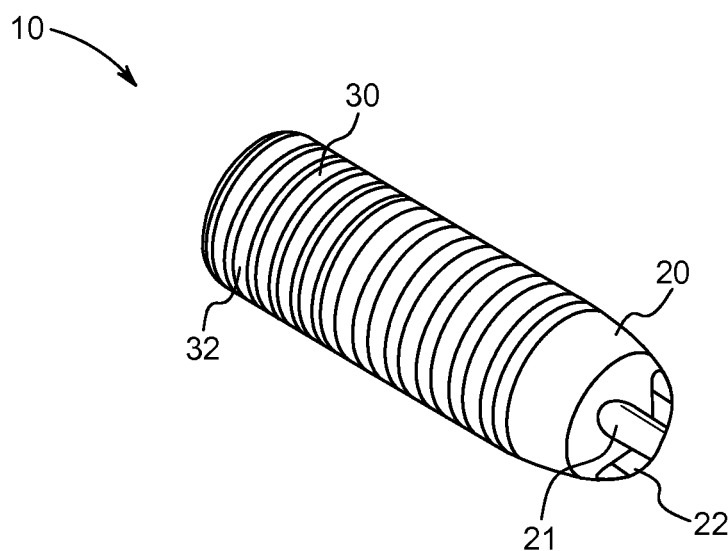
FIG. 1 is a perspective view of a first embodiment of the present invention.

With reference to FIGS. 1-5, a first embodiment suture anchor 10 is illustrated. With reference to FIG. 1, the suture anchor 10 is designed to hold at least two sutures in channels 21 and 22. A single suture can be retained in the channel 21, 22 which is a recessed groove in the tip 20 as illustrated. The tip 20 is an integral portion of the suture anchor body 30. The suture anchor body 30 has external ribs or threads 32 projecting outwardly therefrom. As illustrated, the ribs 32 are spaced from the surface in such a way that they engage the bone for attachment on insertion of the suture anchor 10. Preferably, the suture anchor 10 can be placed in a pre-drilled hole then pressed into position as illustrated.

Figure 2:
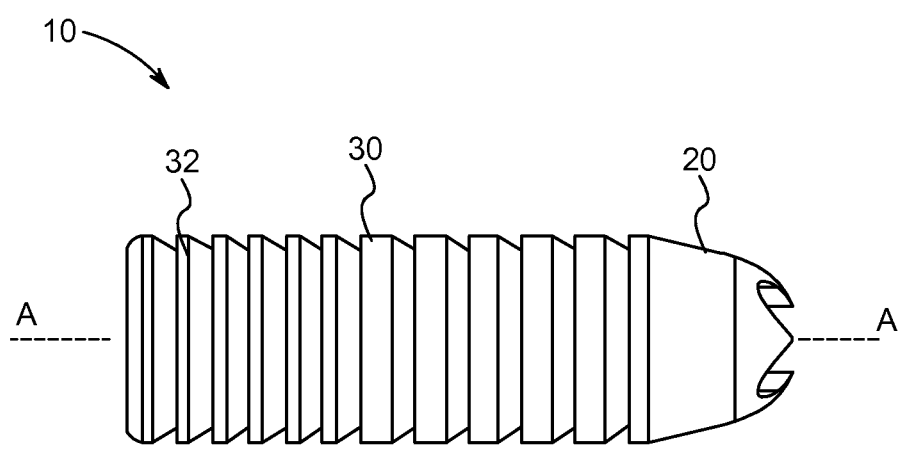
FIG. 2 is a side plan view of the first embodiment.

With reference to FIG. 2, a plan view of the suture anchor 10 is illustrated. In this embodiment, the distal end or tip 20 is illustrated and an axis A is shown extending through the longitudinal length of the body 30.

Figure 3:
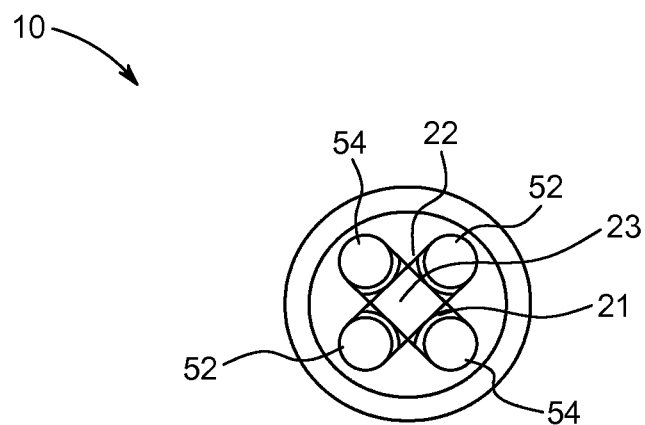
FIG. 3 is an end view showing the external surface of the tip or distal end of the first embodiment.

With reference to FIG. 3, the external surface of the tip 20 is illustrated for the suture anchor 10. As shown, the recess channels 21, 22 are shown crossing in an "X" configuration and intersecting at the location 23. As shown, the recess 21 is cut into the tip 20 to a recess depth of approximately 2.5 mm. The other channel 22 is recessed approximately 1.25 mm deep. The suture channels 21, 22 cross at offset depth levels such that the opening pairs 52 of channel 22 are deeper than the openings 54 of channel 21. Accordingly, as a suture end is either threaded internally and then through and back through an opening 52, 54 depending on the channel in which it resides, the suture is then looped back through the complimentary pair of openings 52, 54 depending on the channel in which it resides in such a way that it is securely positioned and a portion of the suture will lie in the recess preferably at a surface level such that it is at or below the external surface of the tip 20.

Figure 4:
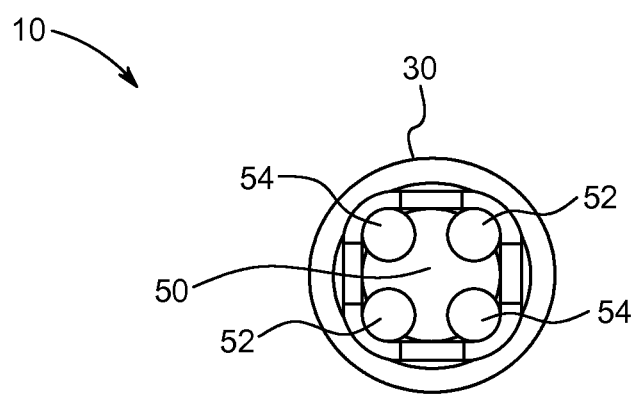
FIG. 4 is an opposite end view showing the internal surface of the tip or distal end and the central opening of the hollow cylindrical body of the first embodiment.

With reference to FIG. 4, the openings 54 are shown and the openings 52 extending into a central opening 50 of the longitudinal body 30. Once the sutures pass from the external surface to the inner opening 50 they can extend outward to the surface wherein soft tissue can be attached using the sutures to affix the suture to the bone anchor when the bone anchor is positioned to a certain depth within a pre-drilled hole.

Figure 5:
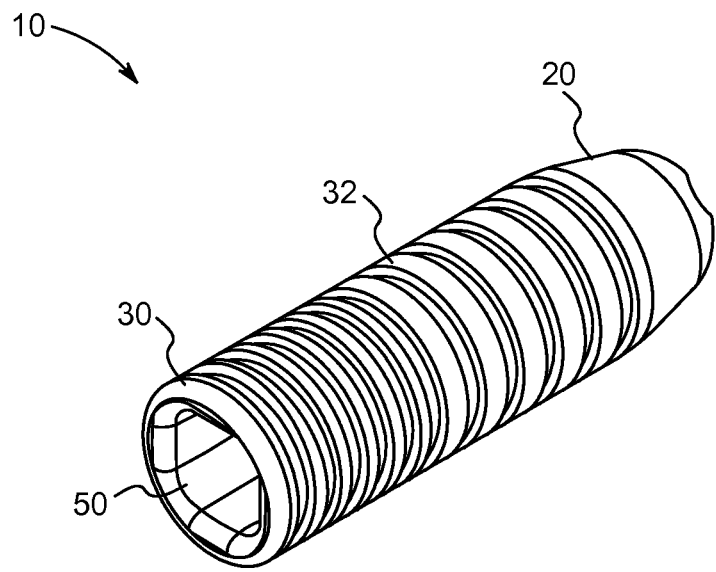
FIG. 5 is a second perspective view of the first embodiment showing the proximal end.
Figure 6:
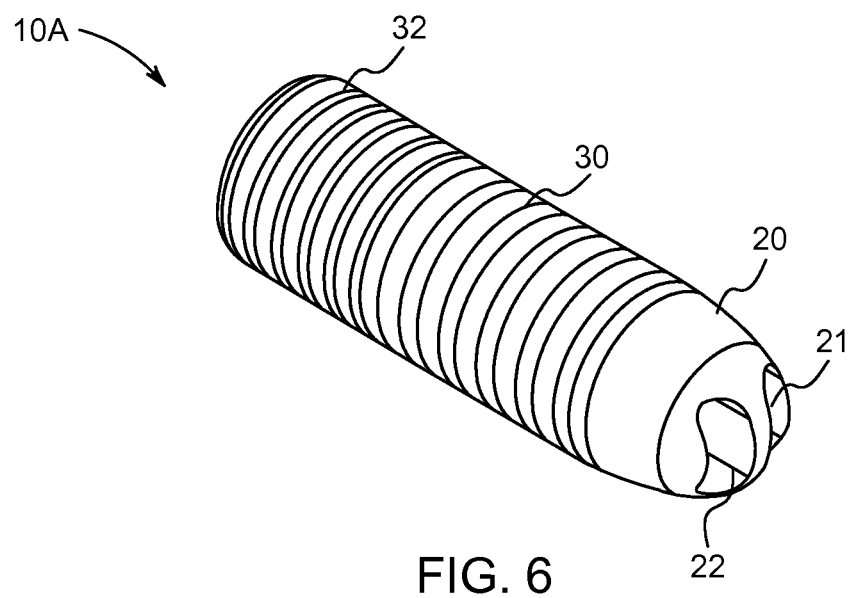
FIG. 6 is a perspective view of a second embodiment of the present invention.
Figure 7:
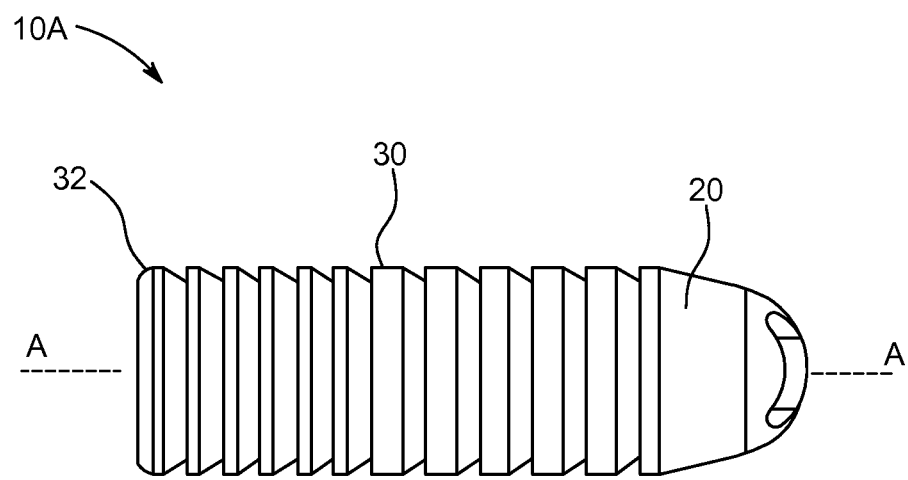
FIG. 7 is a side plan view of the second embodiment.

With reference to FIG. 5, a second perspective view is shown showing the proximal end of the elongated body 30 with the opening 50. At the proximal end of the bone anchor 10 the sutures will extend as indicated when the bone anchor 10 is pushed to a desired depth into the bone opening with the sutures pre-attached they can be used to reattach soft tissue to the anatomically correct location.

With reference to FIG. 2, it is noted that the rib 32 design can be alternated such that they are widely spaced toward the distal tip or end 20 and then more compactly spaced at the proximal end. The proximal end will engage the cortical bone at the surface and therefore can be designed with more ribs 32 so that a tight secure fit can be maintained.

With reference to FIGS. 6-10, a second embodiment of the invention is illustrated. In this embodiment, the suture anchor 10A has channels 21, 22 that are parallel and do not cross the axis A, but are offset a distance relative to the axis A. In this configuration, the channels 21, 22 do not intersect and as such the sutures can be extended through the tip end 20 through the openings 52, 54 as previously discussed. In this case, the portion of the suture that loops through the ends 52 or 54 within each respective channel 21, 22 will lie in the tip preferably at the depth of approximately 1.25 mm in such a fashion that the suture lies at or slightly below the exterior surface of the tip 20. In this fashion, the channels 21, 22 are of equal depth.

Figure 8:
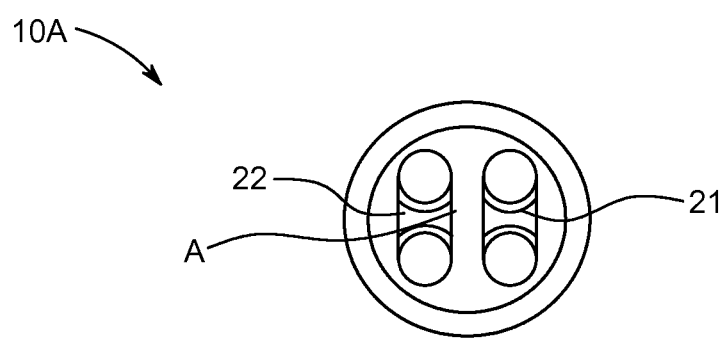
FIG. 8 is an end view showing the external surface of the tip or distal end of the second embodiment.
Figure 9:
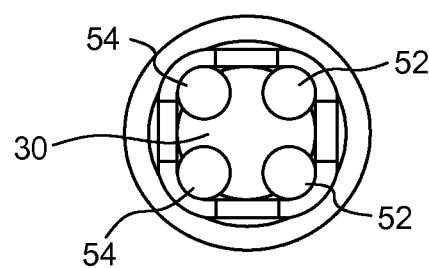
FIG. 9 is an opposite end view showing the internal surface of the tip or distal end and the central opening of the hollow cylindrical body of the second embodiment.
Figure 10:
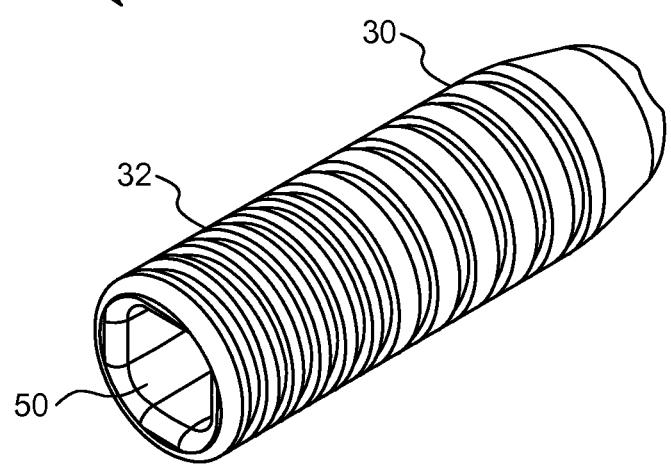
FIG. 10 is a second perspective view of the second embodiment showing the proximal end.

With reference to FIG. 8, the sutures once passed through the openings 52, 54 will extend into the center bore 50 as previously discussed.

The only difference between the first embodiment 10 and the second embodiment 10A as illustrated is that in the second embodiment 10A the sutures lay in channels that are parallel and not in an "X" configuration.

While the bone anchors are shown with ribs 32 that vary along dependent on the longitudinal depth of the anchor 10, 10A; it should be noted that the ribs 32 could all be of equal size, can be of varying depths, to secure the anchor, alternatively, the ribs as shown could be replaced with threads such that the anchor is screwed into position. This can occur easily since the sutures are lying in a recessed channel within the tip and therefore are not prone to being twisted or pulled by the tissue as the anchor is threaded into the pre-drilled opening. As shown, both the first and second embodiments are ideally suited to be placed into a pre-drilled opening through the bone in order to attach to the soft tissue. This can be done as mentioned either by pressing the bone anchor into position or by threading it depending on the configuration of the ribs or threads 32 on the anchor body.

While the present invention is shown for the employment of two sutures, it must be understood that it can be used with a single suture if so desired. However, it is ideally suited to accept two sutures. Accordingly, it is the surgeon's option to use one or two sutures for the attachment of the soft tissue or ligaments to the bone anchor 10, 10A. Other variations are possible with this invention.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A suture anchor comprising;
an entry tip integral to a hollow cylindrical body, the entry tip being at a distal end and the body having a proximal end and projections formed on an external surface of the body for retaining the anchor in a pre-drilled hole formed in bone;
four suture openings formed on the tip at the distal end, each opening being connected to an internal cavity of the body; and
wherein the four suture openings are divided into two pairs, a first pair and a second pair and each first or second pair of two suture openings are recessed in a respective first or second external channel formed in the entry tip, each pair of two suture openings being configured to receive a suture and wherein one of the first external channel or second external channel is deeper than the other so the received sutures are at or below the external surface of the tip adjacent the channels at an intersection.

2. The suture anchor of claim 1 wherein the first external channel and second external channel cross in an "X" configuration intersecting a central axis of the anchor body.

3. The suture anchor of claim 1 wherein each pair of two suture openings can be threaded by a suture such that a suture end or ends of one suture pass and are pulled through the pair of openings holding a portion of the suture lying in one of the first or second external channels and a suture end or ends of another suture cross the other suture passing and pulled through the other pair of openings and a portion of the other suture being held and lying in the other channel, as the ends of both sutures pass through the body opening of the suture anchor past the proximal end.

4. The suture anchor of claim 1 wherein a channel depth at an intersection is equal to the thickness of the crossing sutures.

5. The suture anchor of claim 4 wherein the first or second external channel depth adjacent the intersection is equal to the thickness of a suture being held.

\* \* \* \* \*